United States Patent [19]
Studer

[11] Patent Number: 5,611,909
[45] Date of Patent: Mar. 18, 1997

[54] METHOD FOR DETECTING SOURCE OF ERROR IN AN AMPEROMETRIC MEASURING CELL

[75] Inventor: Matthias Studer, Pansdorf, Germany

[73] Assignee: Drägerwerk Aktiengesellschaft, Lübeck, Germany

[21] Appl. No.: 576,457

[22] Filed: Dec. 21, 1995

[30] Foreign Application Priority Data

Dec. 22, 1994 [DE] Germany .................... 44 45 947.5

[51] Int. Cl.⁶ .................................................. G01N 27/26
[52] U.S. Cl. ................ 205/775; 205/782.5; 205/793; 204/401; 204/415; 204/431; 204/432
[58] Field of Search .................... 204/401, 415, 204/431, 432; 205/775, 782.5, 793

[56] References Cited

U.S. PATENT DOCUMENTS

| | | | |
|---|---|---|---|
| 4,500,391 | 2/1985 | Schmidt et al. | 204/415 |
| 4,614,577 | 9/1986 | Mund et al. | 204/415 |
| 4,961,834 | 10/1990 | Kühn et al. | 204/412 |
| 5,316,648 | 5/1994 | Kühn et al. | 204/415 |

FOREIGN PATENT DOCUMENTS 0419769  4/1991  European Pat. Off. .

*Primary Examiner*—Bruce F. Bell
*Attorney, Agent, or Firm*—Walter Ottesen

[57] ABSTRACT

The invention is directed to a method for detecting error sources in an amperometric measuring cell 1 which includes at least a measuring electrode 2 and a counter electrode 3 within an electrolyte chamber 4 filled with an electrolyte solution 6. A permeable membrane 7 closes off the electrolyte chamber 4 with respect to the measuring sample. The method includes the steps of: providing a voltage source 10 outputting a voltage U to apply across the electrodes to generate a sensor current i(t) between the electrodes; starting with the voltage U across the electrodes at a reference voltage $U_0$ with a reference current $i_0$, increasing or decreasing the voltage U to a first voltage $U_1$ during a first time span $T_1$; shortly after the voltage U assumes the first voltage $U_1$, measuring a first sensor current $i_1$ and/or, toward the end of the first time span $T_1$, measuring a second sensor current $i_2$; and, comparing the sensor currents $i_1$ and/or $i_2$ to the reference current $i_0$.

6 Claims, 3 Drawing Sheets

2

METHOD FOR DETECTING SOURCE OF ERROR IN AN AMPEROMETRIC MEASURING CELL

FIELD OF THE INVENTION

The invention relates to a method for detecting error sources in an amperometric measuring cell which includes at least a measuring electrode and a counter electrode in an electrolyte chamber which is closed by a permeable membrane with respect to the measurement sample to be detected. The measuring cell is connected to a voltage source supplying a voltage and generating a sensor current between the electrodes.

BACKGROUND OF THE INVENTION

An electrochemical measuring cell of the above kind is disclosed in U.S. Pat. No. 4,961,834 incorporated herein by reference. In this measuring cell, a measuring electrode, a reference electrode and a counter electrode are arranged in an electrolyte chamber of the measuring cell housing. The electrolyte chamber is filled with an electrolyte and the housing is closed off by a permeable membrane with respect to the measurement sample to be detected. The measuring electrode, the reference electrode and the counter electrode have respective connecting leads which pass through the measuring cell housing and are connected to an evaluation unit having a voltage source. A sensor current $i(t)$ flows after the electrodes are connected to the voltage source.

It is a disadvantage of the known measuring cell that no information can be obtained from the sensor current $i(t)$ as to the state of use of the measuring cell. Thus, the sensor current $i(t)$ can lie within the predetermined limits but precise concentration measurements are no longer possible.

European patent publication 0,419,769 discloses a method for continuously monitoring an electrode system of potentiometric measurement cells wherein symmetrical bipolar current pulses having different period durations are applied repeatedly to the measuring cell. The voltage change caused thereby, referred to the electrode voltage without current pulse, is compared to a desired value determined experimentally or by computer.

It is a disadvantage of this known method that an additional voltage source is necessary with which the check is carried out. It is also disadvantageous that the check must be carried out at different times and with different period durations in order to detect the individual faults.

SUMMARY OF THE INVENTION

It is an object of the invention to provide a method of detecting error sources for amperometric measuring cells wherein different errors can be detected within a measuring cycle.

The method of the invention is for detecting error sources in an amperometric measuring cell for measuring a sample. The measuring cell includes: an electrolyte chamber having an opening directed toward the sample to be measured and holding an electrolyte; a permeable membrane mounted on the chamber for closing off the chamber; and, a measuring electrode and a counter electrode disposed in the chamber so as to be in spaced relationship to each other. The method includes the steps of: providing a voltage source outputting a voltage $U$ to apply across the electrodes to generate a sensor current $i(t)$ between the electrodes; starting with the voltage $U$ across the electrodes at a reference voltage $U_0$ with a reference current $i_0$, increasing or decreasing the voltage $U$ to a first voltage $U_1$ during a first time span $T_1$; shortly after the voltage $U$ assumes the first voltage $U_1$, measuring a first sensor current $i_1$ and/or, toward the end of the first time span $T_1$, measuring a second sensor current $i_2$; and, comparing the sensor currents $i_1$ and/or $i_2$ to the reference current $i_0$.

The advantage of the invention is seen essentially in that, because of a slight change of the voltage (that is, an increase or a decrease of the voltage to a first voltage $U_1$ during a first time span $T_1$), a change of the sensor current $i(t)$ from $i_1$ to $i_2$ is generated and that the comparison of the first sensor current $i_1$ and/or of the second sensor current $i_2$ to the reference current $i_0$ is utilized to detect a fault in the measuring cell. For carrying out this measurement, a slight alteration of the voltage is sufficient which lies in a range of approximately 0.02 to 1 millivolt. The first time span $T_1$ amounts approximately to 100 milliseconds. If the method of the invention is carried out during gassing of the measuring cell with the measurement sample to be detected, then the reference current $i_0$ is the measurement current and, in a neutral gassing atmosphere, the steady-state sensor base current becomes the reference current.

In an advantageous manner, the voltage is adjusted to a second voltage $U_2$ during a second time span $T_2$ directly after the first time span $T_1$. The second voltage $U_2$ is directed opposite to the first voltage $U_1$ compared to the reference voltage $U_0$. In this way, a polarity reversal is obtained within the measuring cell and the reference current $i_0$ adjusts immediately at the end of the second time span $T_2$ at the measuring cell.

The second time span $T_2$ is so selected that it is equal to or less than 1.5 times the first time span $T_1$.

The second time span $T_2$ is defined by the equation:

$$T_2 = T_1 \times ln(1 - Y \times (1 - 1/X))/ln(X)$$

wherein:

$$X = (i_1 - i_0)/(i_2 - i_0) \text{ and}$$

$$Y = (U_1 - U_0)/(U_2 - U_0).$$

The parameters $C_m$ and $G_m$, which characterize the measuring cell, are computed in accordance with the following equations:

$$G_m = (i_1 - i_0)/(U_1 - U_0)$$

$$C_m = T_1 \times G_m/ln((i_1 - i_0)/(i_2 - i_0)).$$

The parameters $C_m$ and $G_m$ can, for example, be compared to input values $C_{m0}$ and $G_{m0}$ and, when a previously determined limit value is exceeded, an indication is provided that the measuring cell is consumed or damaged and must be exchanged for a new one.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
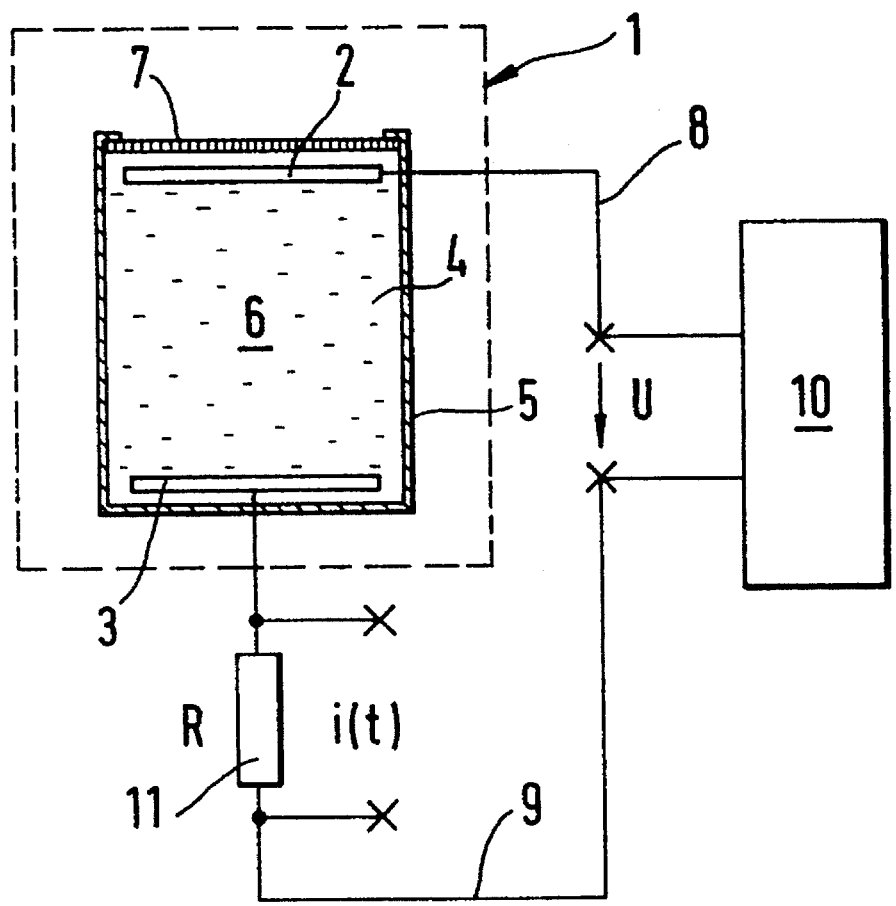
FIG. 1 is a schematic of an amperometric measuring cell having two electrodes.

FIG. 1 shows a schematic configuration of an electrochemical measuring cell 1 having a measuring electrode 2 and a counter electrode 3. The electrodes (2, 3) are arranged in an electrolyte chamber 4 of a housing 5 of the measuring cell 1. The measuring cell housing 5 is filled with an electrolyte 6 in the form of an aqueous solution and is closed off with respect to the gas sample to be detected by a permeable membrane 7. The electrodes (2, 3) are connected via lines (8, 9) to a voltage source 10. A voltage U is applied across the electrodes (2, 3) by means of the voltage source 10. The sensor current i(t) is tapped off as a voltage drop across a measurement resistor 11 in the line 9.

Figure 2:
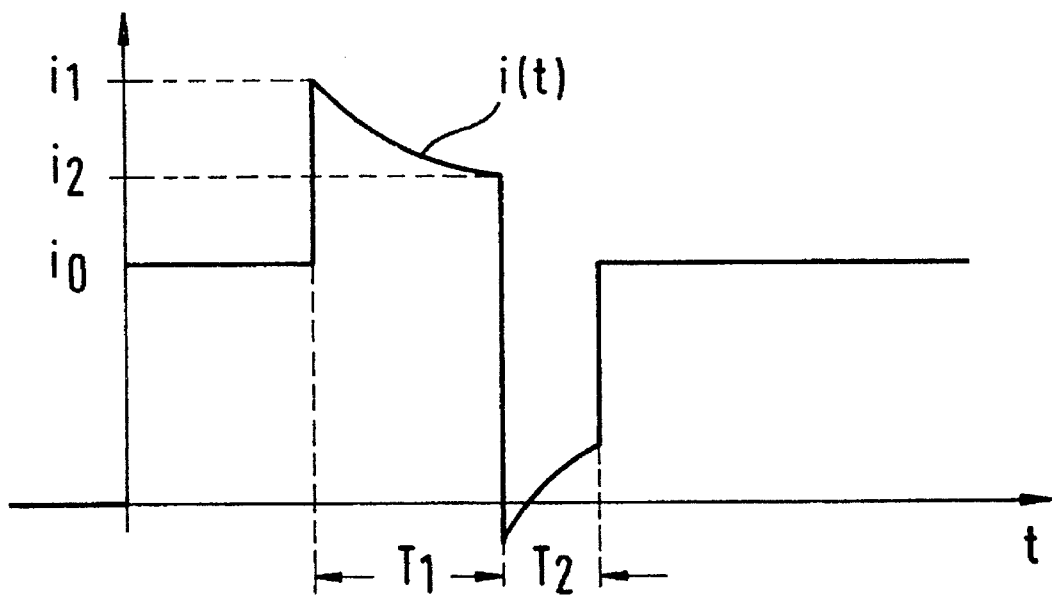
FIG. 2 shows the sensor current $i(t)$ plotted as a function of time when voltages $U_1$ and $U_2$ are sequentially applied.
Figure 2:
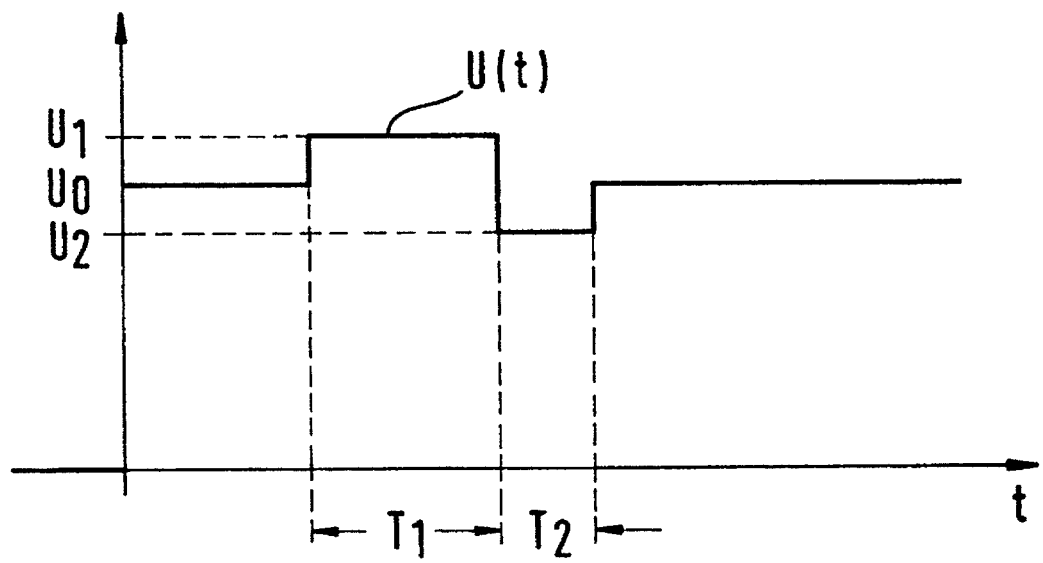

FIG. 2 shows the sensor current i(t) as a function of time (t) and dependent on the voltage U(t). The voltage U is increased to the first voltage $U_1$ during a first time span $T_1$ causing the sensor current i(t) to increase from the reference current $i_0$ to the first sensor current $i_1$ and then drop within the first time span $T_1$ to the second sensor current $i_2$.

A second time span $T_2$ follows directly after the first time span $T_1$. During the second time span $T_2$, the voltage is reduced to the second voltage $U_2$ and the sensor current i(t) drops relative to the reference current $i_0$ and becomes the reference current $i_0$ after the second time span $T_2$. The sensor currents $i_0$, $i_1$ and $i_2$ are read into an evaluation unit (not shown) which contains a microprocessor which compares the sensor currents and carries out the computation operations.

The evaluation unit furthermore controls the changes of the voltage from $U_0$ to $U_1$ and from $U_1$ to $U_2$ and from $U_2$ to $U_0$. The first voltage $U_1$ is adjusted in such a manner that it lies approximately 0.02 to 1 mV above the reference voltage $U_0$ and the duration of the first time span $T_1$ is approximately 100 milliseconds. The duration of the second time span $T_2$ is adjusted in such a manner that it amounts to approximately 0.2 to 1.5 times the first time span $T_1$.

Figure 3:
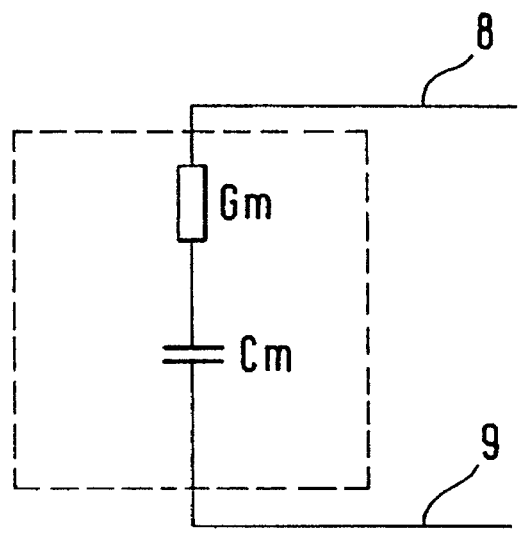
FIG. 3 is an equivalent circuit of the measuring cell of FIG. 1.

The second time span $T_2$ can also be computed from the measured sensor currents $i_0$, $i_1$ and $i_2$ based on a simplified equivalent circuit diagram shown in FIG. 3.

The measuring cell 1 of FIG. 1 can be defined electrically by a measuring electrode capacitor $C_m$ and a measuring electrode conductance value $G_m$. The measuring electrode capacitor $C_m$ is conjointly defined by the measuring electrode 2 and the counter electrode 3 together with the electrolyte 6 disposed therebetween. The measuring electrode conductance value $G_m$ indicates the ohmic resistance between the electrodes (2, 3) and the contact resistances between the electrodes (2, 3) and the leads (8, 9).

The second time span $T_2$ can be computed from the following:

$$T_2 = T_1 \times ln(1 - Y \times (1 - 1/X))/ln(X)$$

wherein:

$$X = (i_1 - i_0)/(i_2 - i_0) \text{ and}$$

$$Y = (U_1 - U_0)/(U_2 - U_0).$$

The measuring electrode capacitance $C_m$ and the measuring electrode conductive value $G_m$ are computed from the following formulas:

$$G_m = (i_1 - i_0)/(U_1 - U_0)$$

$$C_m = T_1 \times G_m/ln((i_1 - i_0)/(i_2 - i_0)).$$

Desired or set values for the measuring electrode capacitance and the measuring electrode conductance are stored in the evaluation unit as reference measuring electrode capacitance $C_{m0}$ and as reference measuring electrode conductance value $G_{m0}$. Within the evaluation unit, a comparison is carried out between the computed parameters $C_m$ and $G_m$ with the desired values $C_{m0}$ and $G_{m0}$.

Deviations of the parameters $C_m$, $G_m$ from the desired values $C_{m0}$ and $G_{m0}$ can have the causes delineated below. Thus, a defective contact of the measuring electrode, for example, affects only the measuring electrode conductance value $G_m$; whereas, a decreasing wetting of the measuring electrode (for example, because of drying out) becomes manifest primarily in the measuring electrode capacitance $C_m$. The tolerance limits for $C_m$ and $G_m$ can be selected to be relatively narrow because the temperature dependency of $G_m$ and $C_m$ is easily determined and can be linearly approximated over a wide range. In this way, not only can a complete failure of the sensor be detected but also changes can be detected which would lead to a failure only later or which would impermissibly affect the measuring characteristics of the sensor.

Figure 4:
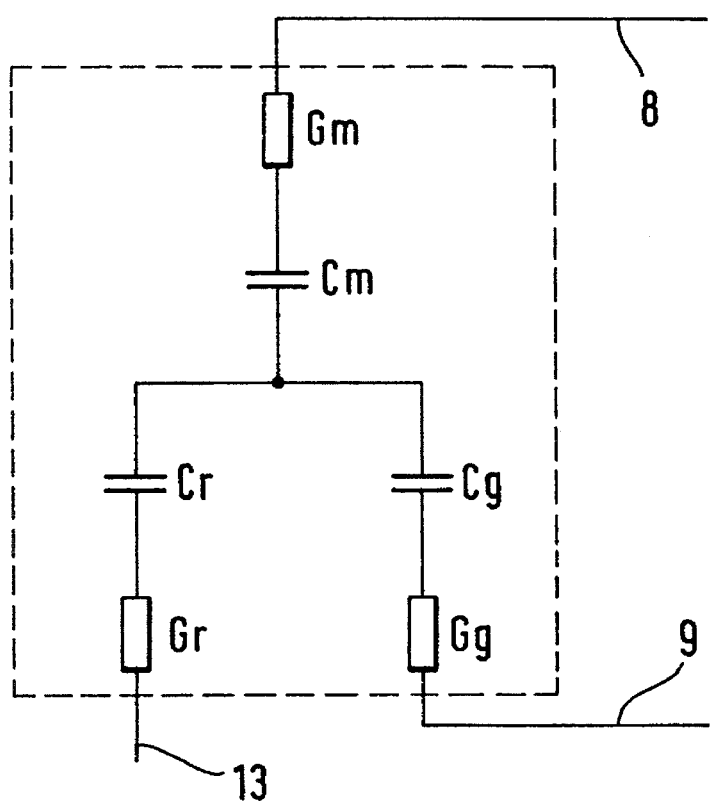
FIG. 4 is an equivalent circuit of a measuring cell incorporating a reference electrode.

The method of the invention for detecting faults is also applicable to a three-electrode measuring cell 12 having a reference electrode. The equivalent circuit diagram of such a sensor is presented in FIG. 4 wherein the same components are identified by the same reference numerals used in FIGS. 1 and 3.

The reference electrode (not shown in FIG. 4) is connected to a line 13. In the equivalent circuit diagram of FIG. 4, $G_g$ identifies the conductance value of the counter electrode, $C_g$ the capacitance of the counter electrode, $G_r$ the conductance value of the reference electrode and $C_r$ the capacitance of the reference electrode. The conductance values can be expressed physically as follows: resistance of the input line to the electrode, transfer resistance of the contact between input line and the electrode and transfer resistance between electrode and electrolyte; and, the capacitors are double layer capacitors between the electrodes.

It is understood that the foregoing description is that of the preferred embodiments of the invention and that various changes and modifications may be made thereto without departing from the spirit and scope of the invention as defined in the appended claims.

What is claimed is:

1. A method for detecting error sources in an amperometric measuring cell for measuring a sample, the measuring cell including: an electrolyte chamber having an opening directed toward the sample to be measured and holding an electrolyte; a permeable membrane mounted on said chamber for closing off said chamber; and, a measuring electrode and a counter electrode disposed in said chamber so as to be in spaced relationship to each other; and, the method comprising the steps of:

providing a voltage source outputting a voltage U to apply across said electrodes to generate a sensor current i(t) between said electrodes;

starting with said voltage U across said electrodes at a reference voltage $U_0$ with a reference current $i_0$, increasing or decreasing said voltage U to a first voltage $U_1$ during a first time span $T_1$;

shortly after said voltage U assumes said first voltage $U_1$, measuring a first sensor current $i_1$ and/or, toward the end of said first time span $T_1$, measuring a second sensor current $i_2$; and, comparing said sensor currents $i_1$ and/or $i_2$ to said reference current $i_0$, wherein the comparison of the sensor currents $i_1$ and/or $i_2$ to the reference current $i_0$ detects a fault in the measuring cell.

2. The method of claim 1, further comprising the step of adjusting said voltage U to a second voltage $U_2$ during a second time span $T_2$ directly after said first time span $T_1$ with said second voltage $U_2$ being directed opposite to said first voltage $U_1$ relative to said reference voltage $U_0$.

3. The method of claim 2, wherein said second time span $T_2$ is equal to or less than 1.5 times said first time span $T_1$.

4. The method of claim 2, said second time span $T_2$ being defined by the equation:

$$T_2 = T_1 \times ln(1 - Y \times (1 - 1/X)/ln(X)$$

wherein:

$$X = (i_1 - i_0)/(i_2 - i_0); \text{ and,}$$

$$Y = (U_1 - U_0)/(U_2 - U_0).$$

5. The method of claim 1, wherein the measuring cell can be defined by an equivalent circuit including parameters $C_m$ and $G_m$ wherein:

$$G_m = (i_1 - i_0)/(U_1 - U_0); \text{ and,}$$

$$C_m = T_1 \times G_m/ln((i_1 - i_0)/(i_2 - i_0)).$$

6. The method of claim 5, further comprising the step of comparing said parameters $C_m$ and $G_m$ to desired or set values $C_{m0}$ and $G_{m0}$, respectively.

* * * * *

UNITED STATES PATENT AND TRADEMARK OFFICE
CERTIFICATE OF CORRECTION

PATENT NO. : 5,611,909
DATED : March 18, 1997
INVENTOR(S) : Matthias Studer

It is certified that error appears in the above-indentified patent and that said Letters Patent is hereby corrected as shown below:

On the title page, in the title, item 54: delete "Source" and substitute -- Sources -- therefor.

In column 1, line 1, in the title: delete "Source" and substitute -- Sources -- therefor.

In column 5, line 22: delete "$T_2 = T_1 \times \ln(1 - Y \times (1 - 1/X)/\ln(X)$" and substitute -- $T_2 = T_1 \times \ln(1 - Y \times (1 - 1/X))/\ln(X)$ -- therefor.

Signed and Sealed this

Twenty-seventh Day of May, 1997

Attest:

BRUCE LEHMAN

Attesting Officer

Commissioner of Patents and Trademarks